(12) United States Patent
Marschke

(10) Patent No.: US 8,546,127 B2
(45) Date of Patent: Oct. 1, 2013

(54) BACTERIA/RNA EXTRACTION DEVICE

(75) Inventor: Dean Marschke, Eden Prairie, MN (US)

(73) Assignee: General Electric Company, Schenectady, NY (US)

( * ) Notice: Subject to any disclaimer, the term of this patent is extended or adjusted under 35 U.S.C. 154(b) by 687 days.

(21) Appl. No.: 12/215,814

(22) Filed: Jun. 30, 2008

(65) Prior Publication Data

US 2009/0325269 A1    Dec. 31, 2009

(51) Int. Cl.
*C12M 1/00* (2006.01)
*C12M 1/34* (2006.01)
*C12N 7/00* (2006.01)
*C12N 7/01* (2006.01)
*C12N 1/00* (2006.01)
*C12N 1/12* (2006.01)
*C12N 1/06* (2006.01)
*B01D 21/24* (2006.01)
*B01D 21/30* (2006.01)

(52) U.S. Cl.
USPC ............... 435/283.1; 435/235.1; 435/254.1; 435/257.1; 435/259; 435/287.2; 210/117; 210/136; 210/257.2; 210/650

(58) Field of Classification Search
USPC .......... 435/283.1, 287.2, 235.1, 254.1, 257.1, 435/259; 210/117, 136, 257.2, 650
See application file for complete search history.

(56) References Cited

U.S. PATENT DOCUMENTS

| | | | |
|---|---|---|---|
| 4,080,294 A | 3/1978 | Edwards et al. | |
| 4,137,169 A | 1/1979 | El-Hindi | |
| 4,358,535 A | 11/1982 | Falkow et al. | |
| 4,478,714 A | 10/1984 | Blake et al. | |
| 4,518,402 A | 5/1985 | Dargel | |
| 4,976,876 A | 12/1990 | Diman et al. | |
| 5,017,292 A * | 5/1991 | DiLeo et al. | 210/645 |
| 5,096,474 A | 3/1992 | Miller, Jr. et al. | |
| 5,155,018 A | 10/1992 | Gillespie et al. | |
| 5,376,527 A | 12/1994 | Robson et al. | |
| 5,423,989 A * | 6/1995 | Allen et al. | 210/650 |
| 5,456,835 A | 10/1995 | Castino et al. | |
| 5,458,782 A | 10/1995 | Hou et al. | |
| 5,620,790 A | 4/1997 | Holzki et al. | |

(Continued)

FOREIGN PATENT DOCUMENTS

| CN | 1606621 A | 4/2005 |
|---|---|---|
| CN | 1886498 A | 12/2006 |

(Continued)

OTHER PUBLICATIONS

Wikipedia Pinch Valve Brochure, printed Jun. 6, 2010, pp. 1-3.*

(Continued)

*Primary Examiner* — Narayan Bhat
(74) *Attorney, Agent, or Firm* — Wegman, Hessler & Vanderburg

(57) ABSTRACT

Apparatus and method for collection of a target material from a liquid sample comprising target species that contain the target material. The apparatus comprises a fluid flow conduit in communication with a filter medium having a pore size adapted to retain target species thereon and pass, as filtrate, lysate containing the desired target material. A lysing agent conduit communicates with the fluid flow conduit and delivers lysing agent to the filter medium to lyse the target cells thereby releasing the desired intracellular target material. The lysing agent may be recirculated through the filter medium for a sufficient time to permit sufficient quantity of lysate to circulate through the system for lysate collection and subsequent assay.

20 Claims, 1 Drawing Sheet

(56) References Cited

U.S. PATENT DOCUMENTS

| | | | |
|---|---|---|---|
| 5,658,714 | A | 8/1997 | Westfall et al. |
| 5,669,946 | A | 9/1997 | Blair, Jr. |
| 5,783,686 | A | 7/1998 | Gonzalez |
| 5,808,041 | A | 9/1998 | Padhye et al. |
| 5,972,613 | A | 10/1999 | Somack et al. |
| 6,011,148 | A * | 1/2000 | Bussey et al. ............... 536/25.4 |
| 6,015,493 | A | 1/2000 | Smith et al. |
| 6,312,588 | B1 | 11/2001 | Conrad et al. |
| 6,383,818 | B1 | 5/2002 | Arai et al. |
| 6,405,875 | B1 | 6/2002 | Cutler |
| 6,479,273 | B1 | 11/2002 | Bogedain et al. |
| 6,508,936 | B1 | 1/2003 | Hassan |
| 6,544,424 | B1 | 4/2003 | Shevitz |
| 6,544,751 | B1 | 4/2003 | Brandwein et al. |
| 6,551,642 | B2 | 4/2003 | Trout |
| 6,821,757 | B2 | 11/2004 | Sauer et al. |
| 6,838,272 | B2 | 1/2005 | Bogedain et al. |
| 6,939,697 | B2 | 9/2005 | Champluvier et al. |
| 6,958,392 | B2 | 10/2005 | Fomovskaia et al. |
| 7,220,549 | B2 | 5/2007 | Buzby |
| 7,252,801 | B2 | 8/2007 | Coffey |
| 7,378,238 | B2 | 5/2008 | Hilbrig et al. |
| 7,385,040 | B2 | 6/2008 | Johansson et al. |
| 2002/0164410 | A1* | 11/2002 | Ogden et al. ............... 426/506 |
| 2003/0064951 | A1 | 4/2003 | Bussey et al. |
| 2003/0201229 | A1 | 10/2003 | Siwak et al. |
| 2004/0076980 | A1 | 4/2004 | Charlton et al. |
| 2004/0245163 | A1 | 12/2004 | Lim et al. |
| 2005/0191619 | A1* | 9/2005 | Davis et al. ............... 435/5 |
| 2005/0244299 | A1* | 11/2005 | Dasgupta et al. ............ 422/68.1 |
| 2007/0003997 | A1* | 1/2007 | Kemmochi et al. ............ 435/34 |

FOREIGN PATENT DOCUMENTS

| | | |
|---|---|---|
| CN | 101113437 A | 1/2008 |
| EP | 00845520 A1 | 7/1983 |
| EP | 0 958 037 B1 | 8/2003 |
| EP | 0 979 237 B1 | 11/2004 |
| EP | 1 710 011 A1 | 10/2006 |
| EP | 0389 063 B2 | 10/2006 |
| EP | 1 624 950 B1 | 7/2007 |
| EP | 1873243 A1 | 1/2008 |
| WO | WO 00/27510 | 5/2000 |
| WO | WO 02/36248 A1 | 5/2002 |
| WO | WO 03/035234 A1 | 5/2003 |
| WO | 2005052137 A1 | 6/2005 |
| WO | WO 2005/115595 A1 | 8/2005 |
| WO | WO 2007/004263 A1 | 1/2007 |
| WO | WO 2007/065229 A1 | 6/2007 |

OTHER PUBLICATIONS

International Search Report issued in connection with corresponding PCT Application No. PCT/US2009/047448 on Oct. 5, 2009.

MSDS No. 301041.233—APTIMA Unisex Swab Specimen Collection Kit, Manufacturer: Gen-Probe Incorporated, San Diego, CA.

MSDS No. 74385—Nonident P40 Substitute, Fluka, Manufacturer: Sigma-Aldrich, Shanghai, China.

Lambert, K.J., "Pretreatment of Cells of 'Klebsiella pneumoniae' with 50% (v/v) Dimethylsulfoxide Yields Purified Deoxyribonucleic Acid of Low Polysaccharide Content", Agric. Biol. Chem., vol. 46, #12, 1982, pp. 3079-3080.

Lytle, C.D., et al., "Virus Passage through Track-Etch Membranes Modified by Salinity and a Nonionic Surfactant", Applied & Environ. Microbiology, vol. 65, #6, Jun. 1999, pp. 2773-2775.

Taylor, M.T., et al., "Lysing Bacterial Spores by Sonication Through a Flexible Interface in a Microfluidic System", Analytical Chemistry, ACS Publications, vol. 73, #3, Feb. 1, 2001, pp. 492-496.

Nishiguchi, M.K., et al., "DNA Isolation Procedures", Methods and Tools in Bioscience and Medicine, 2002, pp. 249-287.

Law, K.A. et al., "Initial investigations into the ultrasonic lysis of microbial cells for the release of adenosine triphosphate", Analytical Biochemistry, vol. 317, 2003, pp. 266-267.

Amari, M. et al., "A Comparison of the Effect of PTFE and UPE Membrane Filters on the Quality of Photoresist Developers", Mykrolis, www.mykrolis.com, 2004, 9 pages.

VanBavel, E., "Effects of Shear Stress on Endothelial Cells: Possible Relevance for Ultrasound Applications", Progress in Biophysics and Molecular Biology, vol. 93, 2007, pp. 374-383.

Morris, D., et al., "Lysate Clearance for Prokaryotic DNA Isolation Using the AcroPrep 96 Filter Plate" Pall Corporation, www.pall.com, 6 pages.

"Assay", Wikipedia, http://en.www.wikipedia.org/wiki/Assay, Apr. 23, 2008, 3 pages.

"Legionella", Wikipedia, http://en.www.wikipedia.org/wiki/Legionella, May 30, 2008, 4 pages.

"RNA", Wikipedia, http://en.www.wikipedia.org/wiki/RNA, Jun. 6, 2008, 6 pages.

U.S. Appl. No. 60/011,148, filed Jan. 4, 2000, Bussey et al.

Search Report issued by the State Intellectual Property Office of the People's Republic of China sent Dec. 27, 2012 for Chinese Patent Application No. CN 200980125281.0 filed Jun. 16, 2009.

First Office Action issued by the State Intellectual Property Office of the People's Republic of China issued Jan. 11, 2013 for Chinese Patent Application No. CN 200980125281.0 filed Jun. 16, 2009.

* cited by examiner

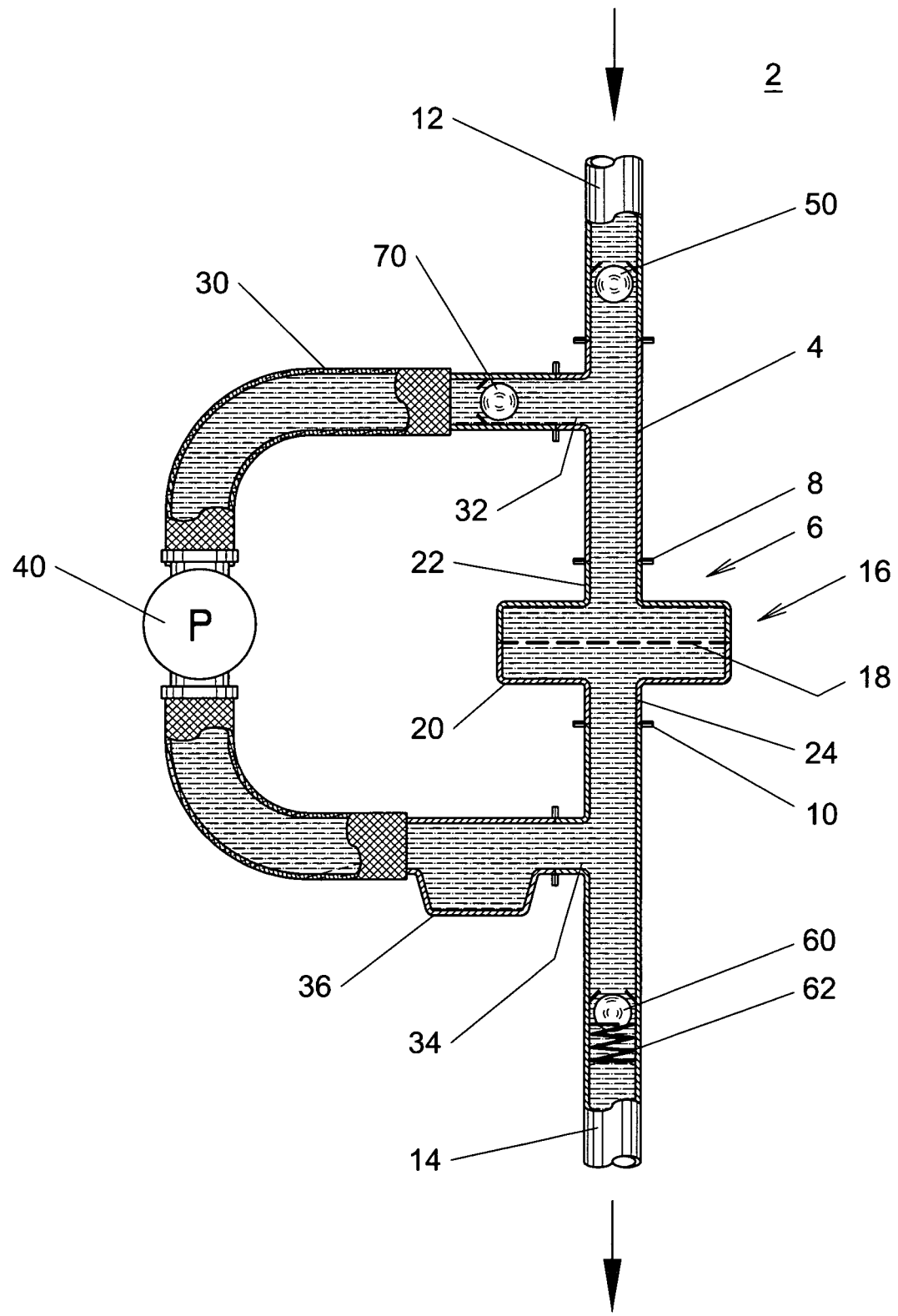

BACTERIA/RNA EXTRACTION DEVICE

FIELD OF THE INVENTION

The present invention relates to a device and method for collecting and lysing microbiological species to release nucleic acids such as RNA and DNA.

BACKGROUND

Detection and control of microorganisms are important in many fields including health care, environmental regulation, bio-warfare, pathogen identification, food and drug testing and in a variety of industrial systems. In industry, presence of undesirable microorganisms decreases the efficiency of operating equipment and ultimately increases the cost of associated goods or services. Furthermore, since microorganisms multiply rapidly, the presence of microbial activity also causes health risks to the public. There is an increasing concern with pathogenic organisms infecting water and process and creating increased human, animal and environmental health risk.

In cooling towers, for example, water borne pathogenic microorganisms, such as *Legionella* sp. may be present. If not properly treated with preferred biocides, aerosolized particles containing the microorganisms can create extreme health concerns from inhalation of the aerosolized microorganisms leading to disease such as Pontiac fever or the sometimes fatal Legionnaire's disease caused by *Legionella pneumophila*. Detection of this and other microorganisms is difficult, especially in the case of open recirculation water systems such as cooling towers because low concentration represent serious health risk and large water volumes must be concentrated into smaller sample volumes in order to perform the desired analytical test and obtain accurate and reproducible results.

SUMMARY OF THE INVENTION

In one aspect, the present invention provides an apparatus for collection of a target material such as a nucleic acid from a liquid sample comprising target species, such as cellular material or viruses, that contain the target material therein. A fluid flow conduit is provided and a filter medium is disposed in contact with the fluid flow conduit. The filter medium has a pore size adapted to retain the target species thereon and pass, as filtrate, lysate containing the target material. Initially, the passage of filtrate is stripped of the target species and would carry non-concentrated quantities of the target material. A lysing agent conduit communicates with the fluid flow conduit and is adapted to deliver lysing agent to the filter medium to lyse the target species thereby releasing the target material.

As used herein, the term "target species" can comprise microbiological organisms such as cellular material and viruses. The cellular material may, for example, be chosen from bacteria, algae, fungi, prokaryotes, etc. As is known, in the cellular organisms, the target material, nucleic acids, such as DNA or RNA, is located inside the cell. In a virus, the target material nucleic acid is located within a protein coat. "Lysing" is then a rupturing of the cell or protein coat to release the target nucleic acid.

Another exemplary embodiment pertains to a method for collecting a desired target material from a liquid sample comprising target species that contain the desired target material therein. The liquid sample is passed through a filter membrane having a pore size adapted to retain the target species thereon and to pass, as filtrate, lysate containing the target material. A lysing agent is brought into contact with the filter membrane and target cells retained thereon thereby rupturing the target cells or protein coat in the case of viral matter to release the target material, such as RNA or DNA. The desired target material passes as filtrate through the filter membrane and may then be collected for analysis.

The invention will be further described in conjunction with the appended drawing.

BRIEF DESCRIPTION OF THE DRAWING

FIG. 1 is a schematic cross-sectional view of an apparatus in accordance with the invention.

DETAILED DESCRIPTION

Turning to FIG. 1, there is shown a disposable device 2 used to capture target species such as bacteria and subsequently lyse the bacteria to remove RNA. The device comprises a main flow conduit 4. The main flow conduit includes an upstream inlet 12 and terminates at downstream outlet 14. A discontinuous segment 6 is provided in the main flow conduit and this discontinuous segment has an upstream fitting 8 and a downstream fitting 10 adapted for snug reception of filter cartridge 16 therein. The fittings can be any one or more of conventional types such as threaded, ball detent, Y-T, hose barb and other fluid tight connectors.

The filter cartridge houses a filter medium 18 therein. As shown, the cartridge comprises a housing 20 preferably composed of a rigid plastic and having an inlet fitting 22 and an outlet fitting 24. The fittings 22, 24 are adapted for snug reception into the upstream fitting 8 and downstream fitting 10 of the main flow conduit. In some cases, it may be desirable to provide a co-or insert molded cartridge wherein the filter is co-or insert molded in the housing.

A recirculation conduit 30 is provided preferably of rubber or similar flexible material. Preferably, the conduit is penetratable by a hypodermic needle or the like. The recirculation conduit 30 sealingly communicates with the main flow conduit 4 at upstream conduit port 32 and downstream conduit port 34. A collection area or reservoir 36 may be provided in the recirculation conduit and is adapted for penetration by a hypodermic syringe or the like so that material may be extracted from the recirculation conduit thereat. Alternatively, a valve may be provided downstream of the filter to provide connection to an extraction tube. A pump 40 is provided in the recirculation conduit and is preferably of a bi-directional peristaltic pump type. Many varied types of pumps can be mentioned as exemplary. A non-direct contact pump is desirable as the recirculation loop may be disposed of after use.

As shown, a recirculation check valve 70 may be provided in the upstream portion of the recirculation conduit. A check valve 50 is also provided at inlet of the main flow conduit and another check valve 60 is provided at the outlet of the conduit 4 and is biased in the closed position via spring 62. The valve 50 may be provided with a spring bias to prevent backflow in the event the recirculation loop was to expand due to any pressure developed to overcome the bias on check valve 60. The position of the exit conduit 14 could be varied from that shown in the drawing to ensure a portion of filtrate, before lysing, is collected in the reservoir to provide a media to be pumped. This way a concentrated lysing agent could be added to the reservoir for injection into the system.

The filter medium 18 is provided with pore sizes chosen so that the desired target species containing the desired target material is captured as retentate thereon. However, after the target species is lysed or ruptured, the target material, such as RNA released from the cells or from a protein coating passes through the membrane as filtrate.

The filter medium 18 can be any of a variety filter membranes designed to retain the desired biological target species thereon. Non-limiting examples of the membrane material comprise nylon, stainless, cellulose ethers, and esters, PTFE, grass fiber, polypropylene, polyvinyl chloride, hydrophilic acrylic copolymer, polyether sulfone, and polycarbonate, etc. Pore sizes of these filters may be on the order of about 10 nm to about 5.0 um. One especially preferred membrane for use in collection of *Legionella pneumophila* cells is a glass fiber membrane available from Millipore having a pore size of about 2.7 um.

It should be mentioned that in another exemplary embodiment of the method, a prefiltering step may be provided wherein, prior to entry into the device 2, the fluid sample may be passed through one or more pre-filters to remove inorganic and large biological components while passing the target species as filtrate. These membranes may, for example, be composed of the same type of materials set forth above for use as the filter medium 18, but pore sizes should be larger, on the order of about 1 to 100 um, more preferably about 1 to 50 um. A tandem filter pair with an upstream filter pore size of about 20 um and a downstream filter pore size of about 11 um may be mentioned as exemplary.

In operation, approximately 500 ml of sample fluid containing target species that in turn, encapsulates the target material, enters through the inlet tube and is passed through the filter capsule. A vacuum or the like may be utilized to assist in drawing the fluid through the filter by applying the vacuum at the outlet port. In one exemplary embodiment, the filter medium is sized to retain *Legionella* bacteria cells yet allow passage of lysed RNA there through.

After the sample is passed through the device, a lysing agent is applied to the system and through the recirculation conduit 30 propelled by the driving action of pump 40. The lysing agent may be admitted through the conduit inlet 12 or it may simply be injected into the recirculation conduit 30 via a syringe or the like. The pump may run in either direction or the pump can be used in combination with an additional check valve to prevent the initial sample from bypassing the filtration device. After a period of time, the lysing buffer or lysing solution from the recirculation conduit ruptures the target species material captured on the filter medium and the lysed cell RNA may then be removed from the device either by using a syringe drawing the fluid directly from the recirculation conduit such as for example at the collection area 36, or, the fluid may be drawn out of the tube outlet. The RNA may then be analyzed by any of a variety of conventional assay techniques. The lysing agent may be applied in several ways. The lysing agent may be inserted through 12, injected into the reservoir 36, or inserted through an additional port added to the loop. If large volumes of lysing agent are applied, check valve 60 may open resulting in loss of target material unless the recirculation loop is evacuated first through a vacuum means as set forth above.

The check valve at the inlet prevents fluid from flowing out of the inlet during the recirculation cycling step and a spring biased check valve at the exit allows the outlet to seal unless slight pressure is applied to draw the fluid out. A spring relief on check valve 50 may also be desirable. Pump 40 is operated so that the pressure generated thereby is such that it does not overcome the outlet spring relief check valve.

As to the lysing agent that is employed, any one that has the effect of rupturing the cell membrane or proteinaceous coating of the virus may be used. Detergents are a non-limiting example of chemicals that are commonly used to disrupt a lipid double layer membrane to release cell contents and lyse membrane protein, and non-limiting examples of lysing chemicals are lithium dodecyl sulfate, CHAPS, Tween-20E, NP40, CTAB, PVPP, Triton X series detergents, sodium cholate, and sodium deoxycholate, guanidinium chloride, or caustic. Chaotropic agents like guanidiunium salts can also act as lysing agents in this system. The lysing efficiency of detergents and alternate lysing agents is dependent on the cell types and specific applications, but all tested materials show adequate lysing within the time requirements for this test method. Enzymes such as lysozymes, mutanolysin, Labiase, lysostaphin, lyticase, proteinase K, endolysin and achromopeptidases may be included as lysing reagents or additives to enhance lysing. Organic solvents, such as DMSO, DMF could be also included as lysing reagents or additives to enhance lysing. A variety of bioscience suppliers offer a wide collection of lysing buffers suitable for cell lysis application. Any physical methods such as shaking, heating cutting and homogenizing, etc., could be added in the process to enhance the lysing efficiency. At present a lysing solution comprising a dilute concentration of lithium lauryl sulfate, nonyl-phenol (40 moles ethoxylation) and DMSO may be mentioned as an exemplary lysing solution that is recirculated through the device.

As above noted, in other varying embodiments, the exit conduit can be positioned to allow air to escape from the reservoir and retain a portion of the fluid filtrate prior to lysing agent application. For example, the exit conduit could be positioned downstream from the filter along the right hand side of the apparatus as shown in the drawing, communicating with conduit 4 and extending angularly upwardly therefrom. Additionally, a separate valve means could be provided in communication with the fluid flow conduit, lysing agent conduit or reservoir to provide for extraction of the desired target material.

While I have shown and described herein certain embodiments of the invention, it is intended that there be covered as well any change or modification therein which may be made without departing from the spirit and scope of the invention as defined in the appended claims.

What is claimed is:

1. An apparatus for collection of a target material from a liquid sample comprising target species that contain said target material therein, said apparatus comprising
   a fluid flow conduit having an upstream inlet and downstream outlet;
   a filter medium between said fluid flow inlet and said downstream outlet; said filter medium having a pore size adapted to retain said target species thereon and pass, as filtrate, lysate containing said target material to a downstream portion of said fluid flow conduit located downstream from said filter medium and upstream from said downstream outlet;
   a lysing agent conduit adapted to deliver lysing agent to said filter medium to lyse said target species thereby releasing said target material, said lysing agent conduit comprising a recirculation conduit means for receiving flow of said filtrate therein and recycling said lysing agent to said filter medium, said recirculation conduit means comprising collection means for collecting said target material therein; and
   a check valve located within said fluid flow conduit and positioned adjacent to one of said upstream inlet or downstream outlet, wherein the check valve is configured to allow fluid flow in only one direction therethrough.

2. The apparatus as recited in claim 1 further comprising a pump operatively connected to said recirculation conduit for pumping said lysing agent to said filter medium and recirculating said lysate through said apparatus.

3. The apparatus as recited in claim 2 wherein said pump comprises a bi-directional pump.

4. The apparatus as recited in claim 1 wherein said fluid flow conduit comprises a discontinuous segment with an upstream fitting and a downstream fitting, said apparatus further comprising a housing containing said filter medium and defining a cartridge with an inlet fitting and an outlet fitting in respective, fluid tight reception in said upstream fitting and said downstream fitting of said discontinuous segment.

5. The apparatus as recited in claim 1 wherein said collection means comprises a collection reservoir having a flexible material therein penetratable by a hypodermic syringe.

6. The apparatus as recited in claim 1 wherein said filter medium comprises pores having sizes ranging from about 10 nm to 5.0 um.

7. The apparatus as recited in claim 6 wherein said filter medium is a fiberglass filter.

8. The apparatus of claim 1, wherein said check valve is positioned adjacent to said downstream outlet.

9. The apparatus of claim 8, wherein said check valve is biased into a closed position.

10. The apparatus of claim 1, wherein said check valve is positioned adjacent to said downstream outlet and a second check valve is located within said fluid flow conduit and positioned adjacent to said upstream inlet.

11. The apparatus of claim 1, wherein a first intersection is formed at a first junction between said recirculation conduit means and said fluid flow conduit adjacent to said upstream inlet, a second intersection is formed at a second junction between said recirculation conduit means and said fluid flow conduit adjacent to said downstream outlet, and said check valve is positioned between said downstream outlet and an intersection of said recirculation conduit means and said fluid flow conduit.

12. An apparatus for collection of a target material from a liquid sample comprising target species that contain said target material therein, said apparatus comprising
    a fluid flow conduit having an upstream inlet and downstream outlet;
    a filter medium positioned between said fluid flow inlet and said downstream outlet, wherein said target species is retainable by said filter medium and a filtrate is passable through said filter medium toward said downstream outlet, said filtrate includes a lysate containing said target material;
    a recirculation conduit for receiving flow of said filtrate therein and recycling said filtrate through said filter medium, said recirculation conduit comprising a collection area for collecting said target material therein; and
    at least one check valve positioned within said fluid flow conduit, wherein said at least one check valve is positioned adjacent to either said upstream inlet or said downstream outlet, wherein the at least one check valve is configured to allow fluid flow in only one direction therethrough.

13. The apparatus of claim 12 further comprising a pump operatively connected to said recirculation conduit for pumping said filtrate through said recirculation conduit to said filter medium.

14. The apparatus of claim 13, wherein said pump comprises a bi-directional pump.

15. The apparatus of claim 12, wherein said fluid flow conduit comprises a discontinuous segment with an upstream fitting and a downstream fitting, said apparatus further comprising a housing containing said filter medium and defining a cartridge with an inlet fitting and an outlet fitting in respective, fluid tight reception in said upstream fitting and said downstream fitting of said discontinuous segment.

16. The apparatus of claim 12, wherein said collection area comprises a collection reservoir having a penetratable flexible material.

17. The apparatus of claim 12, wherein one of said at least one check valve is positioned adjacent to said downstream outlet.

18. The apparatus of claim 12, wherein one of said at least one check valve is positioned adjacent to said downstream outlet and another of said at least one check valve is positioned adjacent to said upstream inlet.

19. The apparatus of claim 12, wherein a first intersection is formed at a first junction between said recirculation conduit and said fluid flow conduit adjacent to said upstream inlet, a second intersection is formed at a second junction between said recirculation conduit and said fluid flow conduit adjacent to said downstream outlet, and said at least one check valve is positioned between either said first intersection and said upstream inlet or said second intersection and said downstream outlet.

20. An apparatus for collection of a target material from a liquid sample comprising target species that contain said target material therein, said apparatus comprising
    a fluid flow conduit having an upstream inlet and downstream outlet;
    a filter medium positioned between said fluid flow inlet and said downstream outlet, wherein said target species is retainable by said filter medium and a filtrate is passable through said filter medium toward said downstream outlet, said filtrate includes a lysate containing said target material;
    a recirculation conduit for receiving flow of said filtrate therein and recycling said filtrate through said filter medium, said recirculation conduit comprising a collection area for collecting said target material therein;
    a pump operatively connected to said recirculation conduit for pumping said filtrate through said recirculation conduit;
    a first check valve positioned within said fluid flow conduit, wherein said first check valve is positioned adjacent to said upstream inlet, wherein the first check valve is configured to allow fluid flow in only one direction therethrough; and
    a second check valve positioned within said fluid flow conduit, wherein said second check valve is positioned adjacent to said downstream outlet, wherein the second check valve is configured to allow fluid flow in only one direction therethrough.

* * * * *